US Patent Lumsden et al.

Patent Number: 4,588,584
Date of Patent: May 13, 1986

[54] **MEDIUM FOR THE ISOLATION OF *PSEUDOMONAS CEPACIA* BIOTYPE FROM SOIL AND THE ISOLATED BIOTYPE**

[75] Inventors: Robert D. Lumsden, Bowie, Md.; Myron Sasser, Newark, Del.

[73] Assignee: The United States of America as represented by the Secretary of Agriculture, Washington, D.C.

[21] Appl. No.: 500,043

[22] Filed: Jun. 1, 1983

[51] Int. Cl.$^4$ .................. A01C 1/06; A01N 63/00; C12N 1/20; C12N 1/28
[52] U.S. Cl. .................................. 424/93; 435/243; 435/249; 435/253; 435/874; 47/57.6
[58] Field of Search .................. 424/93; 435/243, 253, 435/249, 874; 47/57.6

[56] References Cited

U.S. PATENT DOCUMENTS 3,819,829  6/1974  Mann .................................. 424/93

OTHER PUBLICATIONS

Suslow et al., "Rhizobacteria of Sugar Beets . . . ", in Biological Abstracts 74(10)6810, 1982.

Papavizas et al., "Control of Phythium Blight . . . ", Biological Abstracts 65(5)2888, 1977.
Ohh et al., "Evaluating Peas for Resistance to Damping-Off", Biol. Abstr. 67(11) 6944.
Ballard et al., "Taxonomy of the Aerobic Pseudomonads", 1970 J. Gen. Microbiol., vol. 60, 199–214.
Lumsden, Frias, and Sasser, "Ecological Study of *Pseudomonas cepacia* . . . ", Phytopathology, vol. 72, No. 6 1982, p. 709.
Lumsden, Frias, and Garcia, "Biocontrol of Pythium Aphanidermatum on Cucumber . . . ", vol. 72, No. 7 1982, p. 1010.
Burbage et al., "A Medium Selective for *Pseudomonas cepacia*" Phytopathology, vol. 72, No. 6 1982, p. 706.

*Primary Examiner*—Thomas G. Wiseman
*Assistant Examiner*—Elizabeth C. Weimar
*Attorney, Agent, or Firm*—M. Howard Silverstein; William E. Scott; David G. McConnell

[57]  ABSTRACT

A new biotype, SDL-POP-S-1, of the soilborne beneficial bacterium *Pseudomonas cepacia* NRRL B-14149 has been discovered. The biotype is very effective in controlling Pythium diseases of cucumbers and peas. A new medium that is exclusively selective for the bacterium *Pseudomonas cepacia* has also been developed.

3 Claims, No Drawings

MEDIUM FOR THE ISOLATION OF *PSEUDOMONAS CEPACIA* BIOTYPE FROM SOIL AND THE ISOLATED BIOTYPE

BACKGROUND OF THE INVENTION

1. Field of the Invention

This invention relates to the development of a new biotype of the soilborne beneficial bacterium *Pseudomonas cepacia* and to the ability of the new biotype to control Pythium diseases of cucumbers and peas. The invention also relates to a newly formulated medium which is exclusively selective for the bacterium *P. cepacia*.

2. Description of the Art

Biological control is a known approach for insect control. The protection of seedlings from infection by soilborne fungal pathogens by infesting seed with antagonistic microorganisms has also been reported. Many bacteria and fungi antagonistic to foliar pathogens have also been identified.

SUMMARY OF THE INVENTION

An object of this invention is to provide a new biotype of the soilborne beneficial bacterium *Pseudomonas cepacia*.

Another object is to provide a microorganism that is useful for biological control of plant disease.

Still another object is to provide an organism for controlling Pythium diseases of cucumbers and peas.

A further object is to provide a new medium which is exclusively selective for the bacterium *Pseudomonas cepacia*.

According to this invention the above objects are accomplished by a new biotype of the bacterium *Pseudomonas cepacia* designated as SDL-POP-S-1 and the application of the new biotype to control Pythium diseases of cucumbers and peas. The objects were also accomplished by developing a new medium which is exclusively selective for the bacterium *Pseudomonas cepacia* so that the new biotype could be isolated by plating dilutions of soil onto the newly developed medium.

A viable culture of the new biotype of the bacterium *Pseudomonas cepacia* designated as SDL-POP-S-1 has been deposited with the Culture Collection at the Northern Regional Research Center, United States Department of Agriculture, Peoria, Ill., 61604, and its accession number is NRRL B-14149. With reference to 886 OG 638, progeny of this strain will be available during pendency of the patent application to one determined by the Commissioner of Patents and Trademarks to be entitled thereto under 37 CFR §1.14 and 35 USC 122. All restrictions on the availability of progeny of the strain to the public will be irrevocably removed upon the granting of the patent of which the strain is the subject.

DESCRIPTION OF THE INVENTION

The new biotype SDL-POP-S-1, of the soilborne beneficial bacterium *Pseudomonas cepacia* was isolated by use of a newly formulated medium which was found to be exclusively selective for the bacterium *P. cepacia*. The new biotype was isolated by plating dilutions of soil naturally suppressive to diseases caused by the soilborne pathogens *Pythium aphanidermatum* and *P. ultimum* onto the new medium. For the purposes of this invention, it is not necessary to use soil naturally suppressive to *P. aphanidermatum* and *P. ultimum* since Pseudomonas is fairly ubiquitous and is found in many soils. From the large number of potential bacterial colonies that could have developed from the suppressive soil only *P. cepacia* colonies grew on the plate and of these colonies SDL-POP-S-1 was found to have the ability to control Pythium diseases of cucumbers and peas. Damping-off is a well known plant disease caused by Pythium. We found that the new medium was highly selective for the species of bacterium, *Pseuodomonas cepacia*. Twelve isolates of Agrobacterium, Erwinia, Xanthomonas and Pseudomonas failed to grow on the new medium.

The newly developed medium is designated PCAT for *P. cepacia*. The medium consists of (g/L): azelaic acid, 2.0; tryptamine, 0.2; $MgSO_4$, 0.1; $K_2HPO_4$, 4.0; $KH_2PO_4$, 4.0; yeast extract, 0.02; agar, 15.0; and 1 ml of a 1:24 aqueous suspension of chlorothalanil (tetrachloroisophthalonitrile). Following autoclaving for 10 minutes at 121° C., the medium is adjusted to pH 5.7. To prepare PCAT, the $MgSO_4$ is dissolved in distilled water, the azelaic acid is added and the mixture is heated and stirred until it is dissolved. The remaining ingredients are then added.

In order to obtain isolates of *Pseudomonas cepacia* and especially the isolate of this invention, SDL-POP-S-1, one gram of soil in nine ml of phosphate buffered saline (0.1% NaCl in 0.015M $PO_4$ buffer, pH 6.8) was dilution plated onto PCAT. The plates of medium with the soil dilutions was incubated at 39±1° C. Colonies of bacteria that developed on the medium were transferred and later identified by standard bacteriological procedures as *Pseudomonas cepacia*. Biological control ability of the isolates was tested by growing cultures of the isolates on nutrient medium, preparing a slurry of bacterial cells by adding the cells to gum arabic, 30% in water, and coating seeds of pea and cucumber with the preparation. The slurry contained $1 \times 10^7$ bacterial cells for each seed to be coated. The treated pea seeds were planted in soils infested with *Pythium ultimum* and incubated in the greenhouse at 21° C. The treated cucumber seeds were planted in soil infested with *P. aphanidermatum* and incubated at 32° C. After one week, disease incidence was assessed by comparison with non-treated seed planted in the same respective batches of Pythium-infested soils. From these tests we discovered that the isolate designated SDL-POP-S-1 was very effective in controlling Pythium diseases of both peas and cucumbers. For the purposes of this invention, controlling Pythium diseases of peas and cucumbers does not mean preventing the diseases but reducing their incidence by significant amounts.

The effectiveness of the biotype SDL-POP-S-1 in reducing significantly the incidence of Pythium diseases of peas and cucumbers was demonstrated in a number of greenhouse and field experiments. In greenhouse experiments using soil infested with *P. aphanidermatum,* about 26.8% of untreated cucumber seeds produced healthy plants compared to those produced by about 59.3% of treated cucumber seeds. Using soil infested with *P. ultimum,* about 9.2% of untreated pea seeds produced healthy plants compared to those produced by about 56.7% of treated pea seeds. In field experiments in soil infested with *P. aphanidermatum,* about 10.0% of untreated cucumber seeds produced healthy plants compared to those produced by about 34.6% of treated cucumber seeds.

Other methods of utilizing SDL-POP-S-1 such as treating soil instead of seeds with the biotype may prove to be quite effective in controlling Pythium diseases.

We claim:

1. A biologically pure culture of the bacterium *Pseudomonas cepacia* designated as NRRL B-14149.

2. A biocontrol agent for controlling Pythium diseases of peas and cucumbers caused by *Pythium ultimum* and *Pythium aphanidermatum*, respectively, consisting essentially of a biologically pure culture of *Pseudomonas cepacia* NRRL B-14149 and an aqueous solution of gum arabic.

3. A medium selective for *Pseudomonas cepacia* consisting essentially of (g/L): azelaic acid, 2.0 g/L; tryptamine, 0.2 g/L; $MgSO_4$, 0.1 g/L; $K_2HPO_4$, 4.0 g/L; $KH_2PO_4$, 4.0 g/L; yeast extract, 0.02 g/L; agar, 15.0 g/L; and 1 ml/L of a 1:24 aqueous suspension of chlorothalanil.

* * * * *